US 6,716,835 B1

(12) United States Patent
Picaud et al.

(10) Patent No.: US 6,716,835 B1
(45) Date of Patent: Apr. 6, 2004

(54) USE OF DILTIAZEM FOR TREATING RETINAL PATHOLOGIES

(75) Inventors: Serge Picaud, Strasbourg (FR); Maria Frasson, Rouffach (FR); Jose Sahel, Strasbourg (FR); Henri Dreyfus, Strasbourg (FR)

(73) Assignees: INSERM (Institut National de la Sante et de la Recherche Medicale), Paris, Cedex (FR); Universite Louis Pasteur, Strasbourg (FR)

( * ) Notice: Subject to any disclaimer, the term of this patent is extended or adjusted under 35 U.S.C. 154(b) by 0 days.

(21) Appl. No.: 09/806,577

(22) PCT Filed: Oct. 1, 1999

(86) PCT No.: PCT/FR99/02346

§ 371 (c)(1),
(2), (4) Date: Jun. 8, 2001

(87) PCT Pub. No.: WO00/20006

PCT Pub. Date: Apr. 13, 2000

(30) Foreign Application Priority Data

Oct. 2, 1998 (FR) ............................................ 98 12364

(51) Int. Cl.[7] ................................................ A61K 31/55
(52) U.S. Cl. ................................. 514/211.07; 514/912
(58) Field of Search ............................. 514/211.07, 912

(56) References Cited

FOREIGN PATENT DOCUMENTS

| WO | WO 90/06123 | 6/1990 |
| WO | WO 96/00073 | 1/1996 |
| WO | WO 96/03985 | 2/1996 |
| WO | WO 98/50065 | 11/1998 |

OTHER PUBLICATIONS

XP–002105534, Deepak Edward et al. "Amelioration of Light–Induced Retinal Degeneration by a Calcium Overload Blocker", pp. 554–562.
XP–002105535, Deepak Edward et al., "The Amelioration of Light Induced Retinal Degeneration by Flunarizine, a Calcium Channel Blocker", pp. 1441–20.
XP–002105536, Iman Sahly et al., "Calcium Channel Blockers Inhibit Retinal Degeneration in Retinal–Degeneration–B Mutant of Drosophila", pp. 435–439.
XP–002105537, Mark Tso, "In Search of Pharmacotherapy For Photoreceptor Degeneration".
XP–002105538, Carlos Medrano et al., "Oxygen Consumption in the Rat Outer and Inner Retina: Light–and Pharmacologically–Induced Inhibition", pp. 273–284.
XP–002105539, David Zava et al., "Cyclic GMP Accumulation Causes Degeneration of Photoreceptor Cells: Simulation of an Inherited Disease", pp. 664–666.
XP–002105540, Jeffrey Stern et al., "Control of the Light–Regulated Current in Rod Photoreceptors by Cyclic GMP, Calcium and L–CIS–Diltiazem", pp. 1163–1167.
XP–002105541, Basil Pawlyk et al., "Effects of IBMX on the Rod ERG of the Isolated Perfused Cat Eye: Antagonism With Light, Calcium of L–CIS–Diltiazem", pp. 1093–1097.

*Primary Examiner*—Zohreh Fay
(74) *Attorney, Agent, or Firm*—Young & Thompson

(57) ABSTRACT

The invention concerns the use of a calcium channel blocker compound and/or cyclic GMP-dependent channels, namely diltiazem, for treating retinal pathologies, and more particularly retinal diseases caused by degeneration of visual receptors, in a human or animal.

20 Claims, 3 Drawing Sheets

USE OF DILTIAZEM FOR TREATING RETINAL PATHOLOGIES

The present invention concerns the use of blocker compounds of calcium channels and/or channels activated by 3'5' cyclic guanosine monophosphate (cGMP), in the field of treating retinal pathologies, and more particularly retinal diseases resulting from photoreceptor degeneration, in humans or animals, such as retinitis pigmentosa or other pathologies substantially involving the photoreceptors, especially age-related macular degeneration.

BACKGROUND OF THE INVENTION

Retinitis pigmentosa designates a group of these degenerative diseases of the photoreceptors (Berson, 1996) leading to blindness.

Numerous mutations affecting various rod proteins, and potentially the cause of this disease, have been described. Among these mutations can be mentioned those affecting the genes of proteins implicated in the phototransduction cascade, such as rhodopsin, transducin, phosphodiesterase, arrestin, or structural proteins such as peripherin.

The rd (retinal degeneration) mouse has been studied for more than 70 years as a model of retinitis pigmentosa (Farber et al., 1994), inasmuch as the process of retinal degeneration is similar to that observed in the pigmentary retina, the death of the retinal rods being followed by an unexplained loss of the retinal cones. Moreover, the causal mutation was localized in the gene encoding the β sub-unit of cGMP-phosphodiesterase (PDE) (Bowes et al., 1990), as in certain families affected by the disease (McLaughlin et al., 1993).

PDE is activated during the phototransduction cascade by the α chain of transducin, itself activated by light-stimulated rhodopsin. Activated PDE hydrolyzes cGMP, thus reducing the concentration of cGMP and hence the number of open cGMP-dependent channels, the final consequence being a decrease in the conductance of cations such as $Na^+$ and $Ca^{2+}$ and in turn a reduction of the depolarization current of the photoreceptors into obscurity. In the rd mouse, Farber and Lolley (1974) have shown that an abnormal increase of the cGMP concentration precedes the degeneration of the photoreceptors. The toxicity of cGMP at high concentrations was next established for normal photoreceptors (Lolley and Farber, 1977; Ulshafer et al., 1980).

Several therapeutic approaches intended to prevent photoreceptor loss are at present undergoing investigation in rd mice. It was therefore described that in vivo gene therapy permits retarding a death of photoreceptors for six weeks after sub-retinal injection of a replication-deficient recombinant adenovirus which contains the cDNA encoding murine PDE (Bennett et al., 1996). Photoreceptor transplantation (Gouras et al., 1994, Silverman et al., 1989) was described as permitting preservation of the cone photoreceptors (Mohand-Said et al., 1997). The interpretation of this effect in terms of the paracrine mechanism agrees with the increase of the photoreceptor survival observed in coculture with healthy photoreceptors (Mohand-Said et al., 1998) or after in vivo or in vitro application of trophic factors such as fibroblast or neuronal growth factors (LaVail et al., 1998).

Nevertheless, no treatment for retinal diseases resulting from photoreceptor degeneration is available at present, apart from prescription of vitamin A for retinitis pigmentosa (Berson, 1996).

BRIEF SUMMARY OF THE INVENTION

The present invention particularly concerns providing pharmaceutical compositions that can be used in the field of treating retinal diseases resulting from photoreceptor degeneration in humans or animals.

DETAILED DESCRIPTION OF THE INVENTION

Specifically, the present invention arises from the demonstration by the inventors of the fact that blocker compounds of calcium channels and/or cGMP-dependent channels, such as diltiazem hydrochloride, permit not only retarding degeneration of the rods and the cones in the rd mouse, but also preserving the capacity of the retinal cells to respond to luminous stimuli.

Thus, the present invention concerns the use of calcium channel and/or cGMP-dependent channel blocker compounds for preparing a medicament intended for the treatment of pathologies related to photoreceptor degeneration of the retina, and more particularly retinitis pigmentosa, or pathologies substantially involving the photoreceptors, such as age-related macular degeneration.

By calcium and/or cGMP-dependent channel blockers, is meant any compound capable of reducing the ionic conductance of these channels.

The invention more particularly concerns the use of diltiazem (D-cis-enantiomer), L-cis-enantiomer, their metabolites and their pharmaceutically acceptable salts, for preparing a medicament intended for treating pathologies related to photoreceptor degeneration of the retina, especially to the treatment of retinitis pigmentosa, or substantially involving the photoreceptors, such as age-related macular degeneration.

The invention more particularly concerns the above-mentioned use of diltiazem of the formula

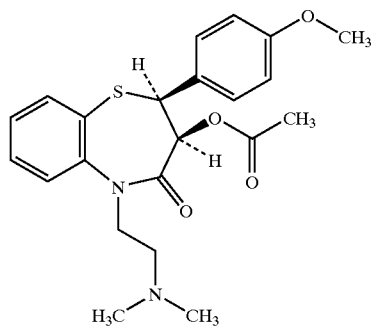

as well as its pharmaceutically acceptable acid addition salts, especially the malate or hydrochloride of diltiazem.

The invention also concerns the above-mentioned use of the L-cis-enantiomer of diltiazem, or the racemate of diltiazem, as well as their pharmaceutically acceptable acid addition salts, especially the hydrochloride of the cis-isomer of the following formula:

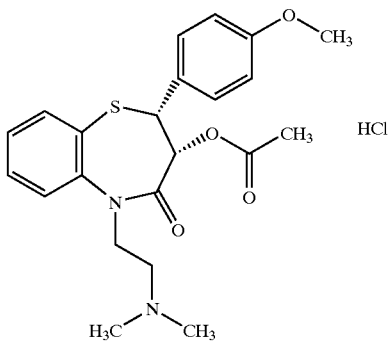

The invention also concerns the above-mentioned use of one of the metabolites of diltiazem, as well as their pharmaceutically acceptable acid addition salts, responding to the following formulae:

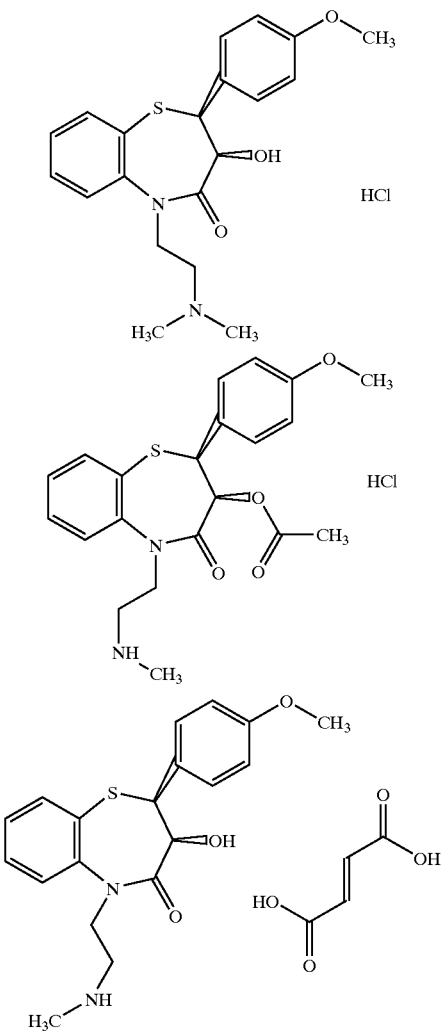

Advantageously, the calcium and/or cGMP-dependent channel blockers mentioned above are used for preparing pharmaceutical compositions present in a form that can be administered by any route, especially orally, intra-muscularly, intravenously, intra-ocularly, or in the form of eye drops.

Preferably, the pharmaceutical compositions of the invention comprise, in unit form, about 0.1 to about 100 mg of a calcium and/or cGMP-dependent channel blocker, as defined above, in association with a pharmaceutically acceptable vehicle.

Figure 1:
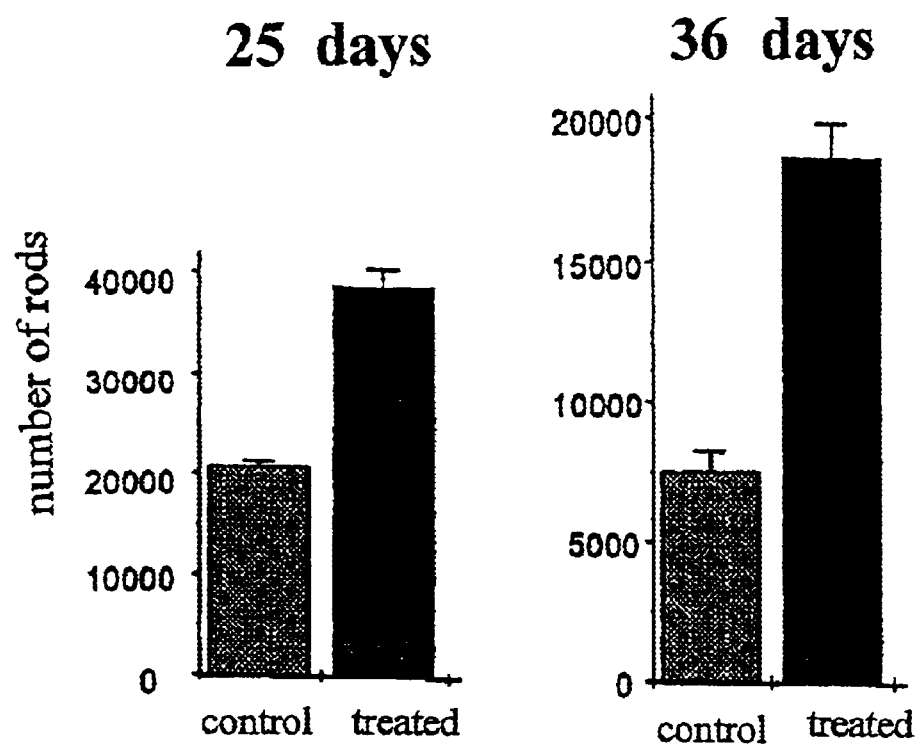
FIG. 1: estimation of the number of rods in the entire retinas of rd mice at 25 days and at 36 days after treatment with diltiazem hydrochloride, relative to untreated control rd mice.
Figure 2:
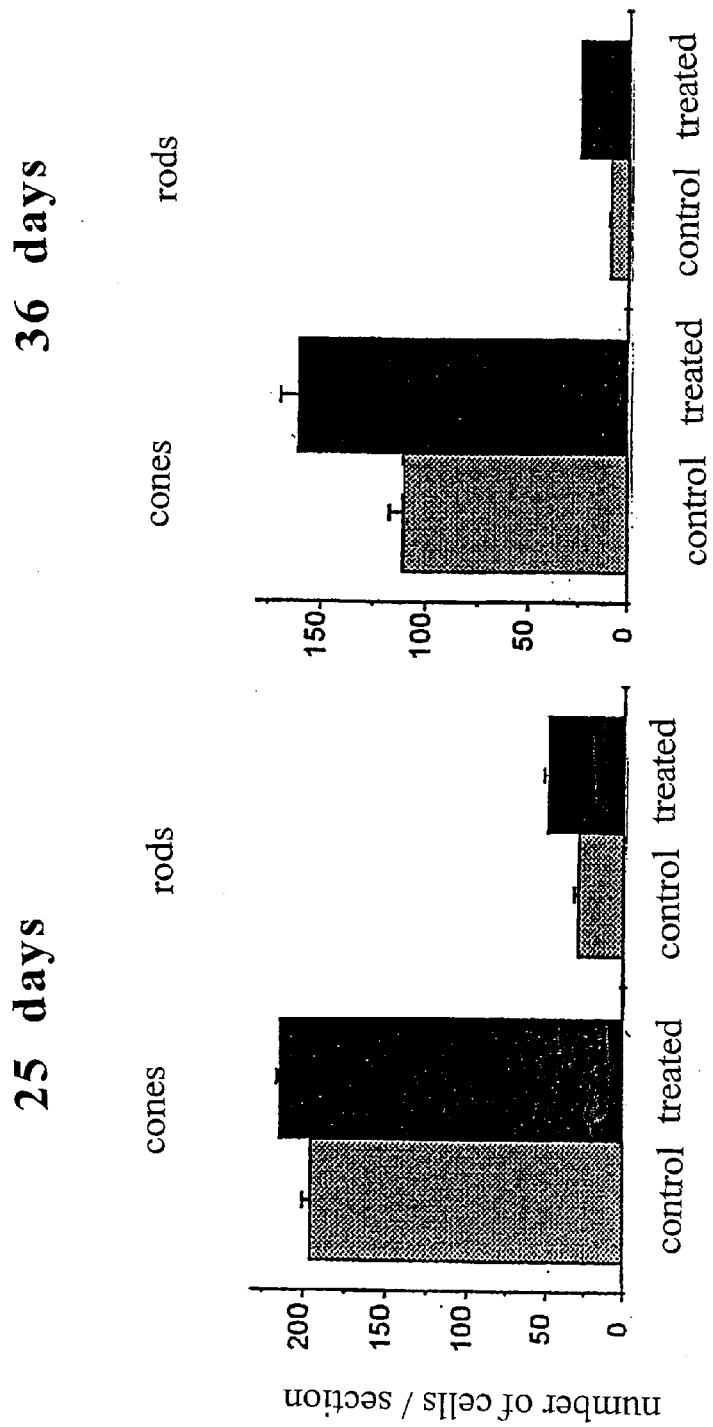
FIG. 2: estimation of the number of cones and rods in retinal sections of rd mice at 25 days and 36 days, treated with diltiazem hydrochloride, relative to untreated control rd mice.
Figure 3:
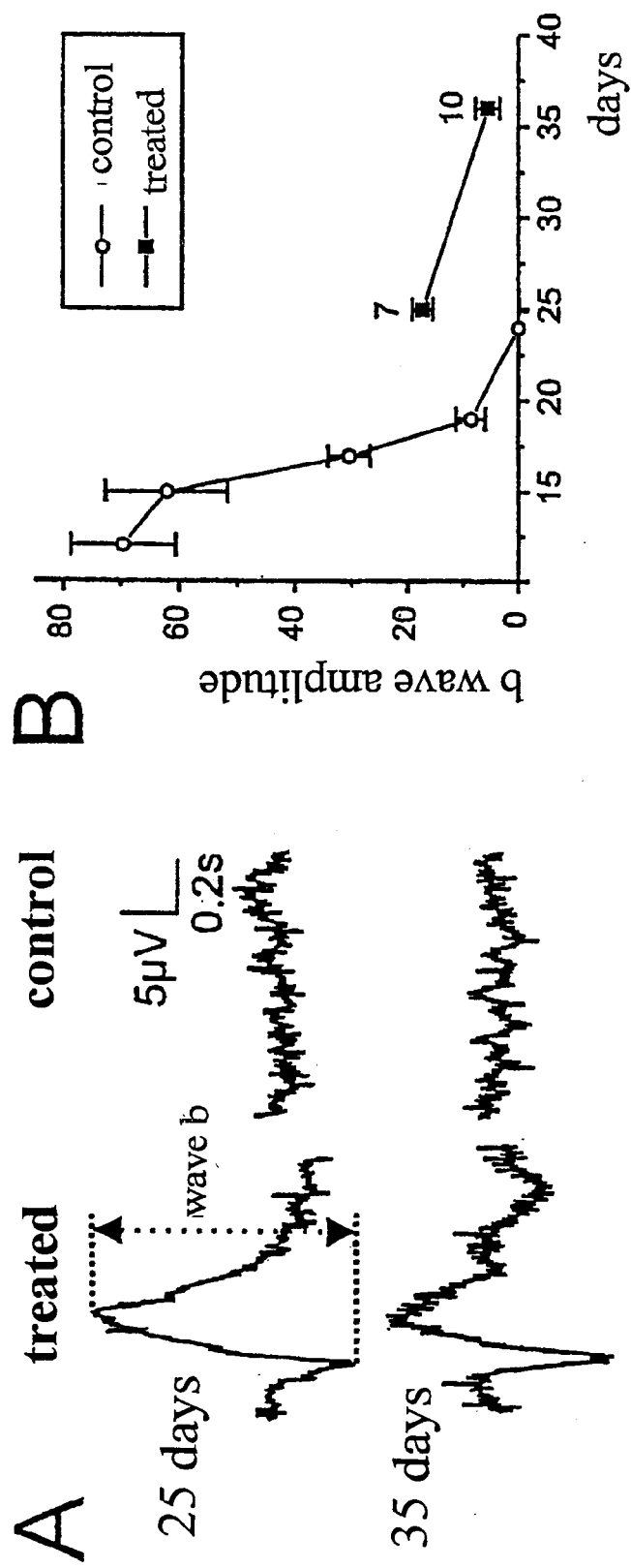
FIG. 3: effect of diltiazem hydrochloride on ERG measurements in rd mice. A) depiction of the ERG recordings measured in control and treated rd mice at 25 and 36 days after birth. B) effect of diltiazem hydrochloride on the b wave of ERG; the curve corresponding to measurement of the b wave amplitude as a function of time in control rd mice is shown by empty circles, whereas that corresponding to the same measurement in the rd mice treated with diltiazem hydrochloride is shown by black squares.

The invention will be better understood from the following FIGS. 1 to 3.

FIG. 1 illustrates the rod survival at the 25th day and at the 36th day after birth of rd mice treated with diltiazem hydrochloride. The injections of diltiazem hydrochloride are initiated at the 9th day after birth, which corresponds to the time when the first signs of rod degeneration appear. The doses of diltiazem hydrochloride (2.5 mg/ml in a physiological solution) are gradually increased from 50 µl per day up to 100 µl twice daily, according to the growth of the animal. Since the electroretinograms (ERG) are taken before sacrificing the animals, the last injection was given 48 hours before the physiological measurement. After fixation of the retina, the rods are marked by anti-rhodopsin antibody (4D2-rho). (Hicks and Molday, 1986) and a number was estimated by stereology on the flattened retinas using a random sampling technique (Mohand-Said et al., 1988). Only the right retinas are taken into consideration, so as to obtain independent results. Treatment with diltiazem hydrochloride increased the rod survival by 86% on the 25th day, and by 148% on the 36th day in treated animals relative to the control rd mice. Repeated injections of physiological solution alone had no significant effect on the survival of the rods (7416±1291, s.e.m., n=5) with respect to untreated animals (7648±774, s.e.m., n=4). These observations therefore show that treatment of rd mice with diltiazem hydrochloride induces rod survival.

FIG. 2 illustrates the survival of the cones at the 25th day and at the 36th day after birth, in rd mice treated with diltiazem hydrochloride. The number of cones was estimated indirectly after coloration of the nuclei with DAPI (4',6-diamino-2-phenylindole) on retinal sections. To obtain this number, the number of immunomarked rods was subtracted from the number of photoreceptor nuclei marked with DAPI. Treatment with diltiazem hydrochloride increased by 109% the survival of the cones at the 25th day, and by 144% at the 36th day in the treated animals, relative to the control rd mice.

FIG. 3 illustrates the fact that the survival of the photoreceptors is accompanied by physiological improvements in the rd mice treated with diltiazem hydrochloride. This demonstration was performed by ERG measurements in the treated rd mice and the control rd mice. In the untreated rd mice, the amplitude of the a and b waves of the ERG decrease regularly from the 12th day after birth until extinction at the 24th day after birth. In contrast, all of the treated animals display ERG signals at the 25th day after birth (n=7). At the 36th day after birth, 4 out of 10 treated animals display ERG signals that can be measured in both eyes. These observations demonstrate that treatment with diltiazem hydrochloride not only permits rod survival but also protects the visual functions of the retina.

REFERENCE BIBLIOGRAPHY

Bennett J., Tanabe T., Sun D., Zeng Y., Kjeldbye H., Gouras P., Maguire A. M.; "Photoreceptor cell rescue in retinal degeneration (rd) mice by in vitro gene therapy", Nat. Med. (1996) 2:649–654.

Berson E. L.; "Retinitis pigmentosa: Unfolding its mystery", Proc. Natl. Acad. Sci. (1996) 93: 4526–4528.

Bowes C., Li T., Danciger M., Baxter L. C., Applebury M. L., Farber D.; "Retinal degeneration in the rd mouse is caused by a defect in the β-subunit of rod cGMP-phosphodiesterase"; Nature (1990) 347: 677–680.

Farber D. B. and Lolley R. N.; Cyclic guanoside monophosphate: Elevation in degenerating photoreceptor cells of the C3H mouse retina. Science (1974) 186: 449–451.

Farber D. B., Flannery J. G., Bowes-Rickman C.; "The rd mouse story: seventy years of research on an animal model of inherited retinal degeneration", Prog. Ret. Eye Res. (1994) 31–62.

Gouras P., Du J., Kjeldbye H., Yamamoto S., Zack D.J.; "Long-term photoreceptor transplants in dystrophic and normal mouse retina", Invest. Ophthalmol. Vis. Sci. (1994) 35: 3145–53.

Hicks D. and Molday R. S.; Differential immunogold-dextran labeling of bovine and frog rod and cones cells using monoclonal antibodies against bovine rhodopsin. Experimental Eye Research (1986) 42: 55–71.

Lavail M. M., Yasumura D., Matthes M. T., Lau-Villacorta C., Unoki K., Sung C. H., Steinberg R. H. Protection of mouse photoreceptors by survival factors in retinal degenerations. Invest. Ophthal. Vis. Sci. (1998) 39: 592–602.

Lolley R. N., Farber D. B., Rayborn M. E. and Hollyfield J. G.; Cyclic GMP accumulation causes degeneration of photoreceptor cells: simulation of an inherited disease. Science (1977) 196: 664–666.

McLaughlin M. E., Sandberg M. A., Berson E. L., Drya T. P.; "Recessive mutations in the gene encoding the b-subunit of rod phosphodiesterase in patients with retinitis pigmentosa", Nature genetics (1993) 4: 130–133.

Mohand-Said S., Hicks D., Simonutti M., Tran-Minh D., Deudon-Combe A., Dreyfus H., Silvermann M. S., Mosinger Ogilvie J., Tenkova T., Sahel J.; "Photoreceptor transplants increase host cone survival in the retinal degeneration (rd) mouse", Ophth. Res. (1997) 29: 290–297.

Mohand-Said S., Deudon-Combe A., Hicks D., Simonutti M., Forster V., Fintz A. C., Léveillard T., Dreyfus H. and Sahel J.; Normal retina releases a diffusible factor stimulating cone survival in the retinal degeneration mouse. Proceeding of the National Academy of Sciences (USA) (1998) 95: 8357–8362.

Ulshafer R. J., Garcia C. A. and Hollyfield J. G.; Sensitivity of photoreceptors to elevated levels of cGMP in the human retina. Investigative Ophthalmology and Visual Science (1980) vol. 19, n° 10: 1236–1241.

What is claimed is:

1. A method of retarding degeneration of retinal photoreceptors comprising administering to a patient afflicted with age-related macular degeneration or retinitis pigmentosa a therapeutically effective amount of a compound selected from the group consisting of diltiazem (D-cis-enantiomer), L-cis-enantiomer, their metabolites and their pharmaceutically acceptable salts, said amount being effective to retard degeneration of retinal photoreceptors.

2. A method of treating age-related macular degeneration or retinitis pigmentosa, comprising administering to a patient in need of such treatment a therapeutically effective amount of a compound selected from the group consisting of diltiazem (D-cis-enantiomer), L-cis-enantiomer, their metabolites and their pharmaceutically acceptable salts, said amount being effective to retard degeneration of retinal photoreceptors.

3. The method according to claim 1 wherein said compound has the formula

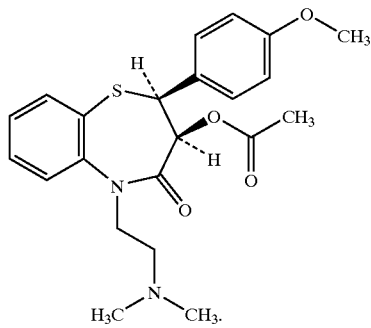

4. The method according to claim 1 wherein said compound has the formula

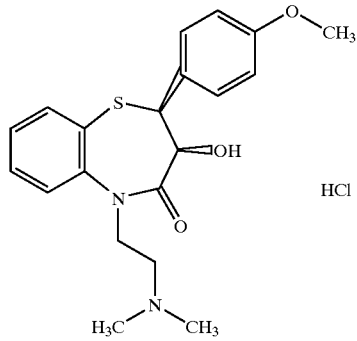

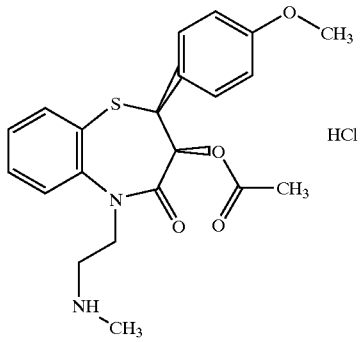

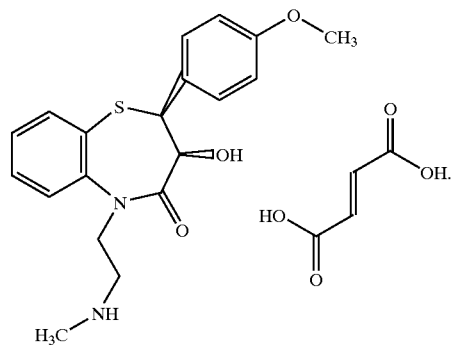

5. The method according to claim 1 wherein said compound has the formula

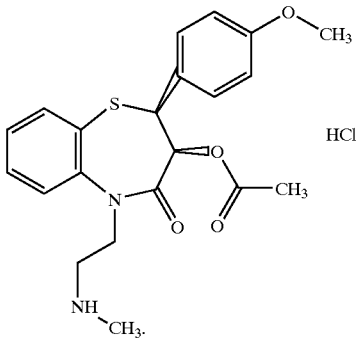

6. The method according to claim 1 wherein said compound has the formula

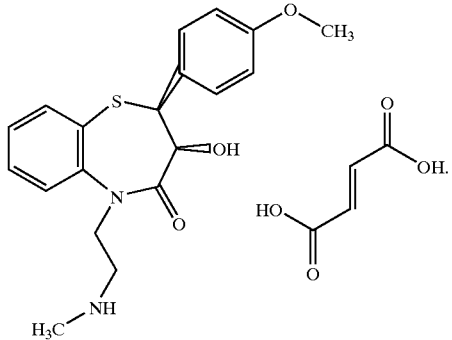

7. The method according to claim 1, further comprising preparing a medicament with said compound;
said medicament being administrable orally, intramuscularly, intravenously, intra-ocularly, or in the form of eye drops.

8. The method according to claim 1 wherein said pharmaceutically acceptable salt is a pharmaceutically acceptable acid addition salt selected from the group of malate or hydrochloride.

9. The method according to claim 2 wherein said compound has the formula

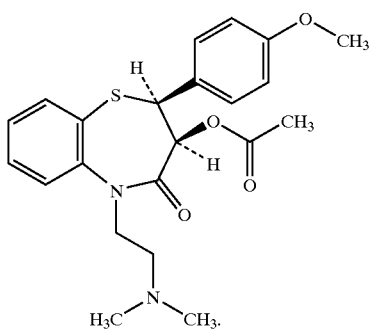

10. The method according to claim 2 wherein said compound has the formula

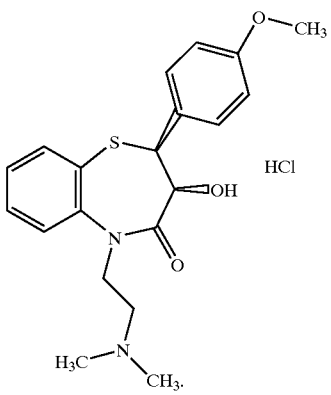

11. The method according to claim 2 wherein said compound has the formula

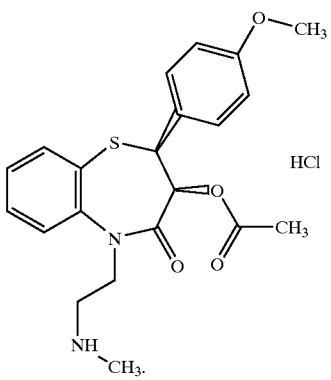

12. The method according to claim 2, wherein said compound has the formula

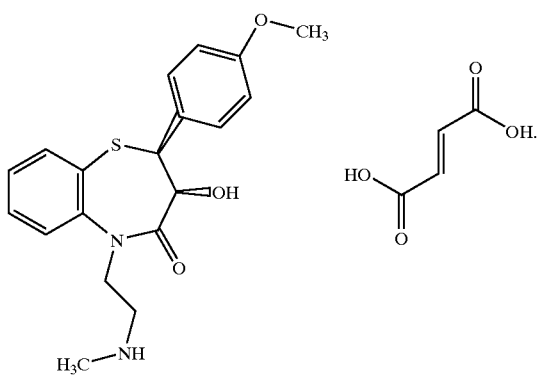

13. The method according to claim 2, further comprising preparing a medicament with said compound;
said medicament being administrable orally, intramuscularly, intravenously, intra-ocularly, or in the form of eye drops.

14. The method according to claim 2 wherein said pharmaceutically acceptable salt is a pharmaceutically acceptable acid addition salt selected from the group of malate or hydrochloride.

15. A method of treating retinitis pigmentosa comprising administering to a patient in need of such treatment a therapeutically effective amount of diltiazem (D-cis-enantiomer), an L-cis-enantiomer of diltiazem, racemates of diltiazem, metabolites of diltiazem, or pharmaceutically acceptable salts of diltiazem, said amount being effective to retard degeneration of retinal photoreceptors.

16. The method according to claim 15 wherein said compound has the formula

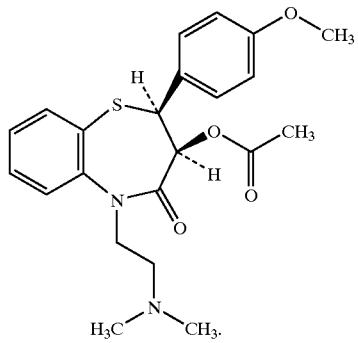

17. The method according to claim 15 wherein said compound has the formula

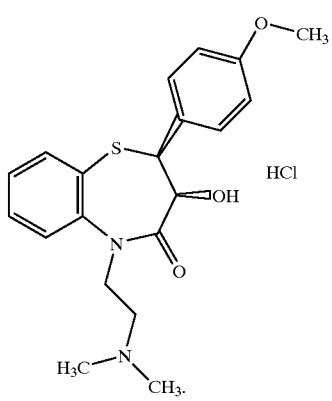

18. The method according to claim 15 wherein said compound has the formula

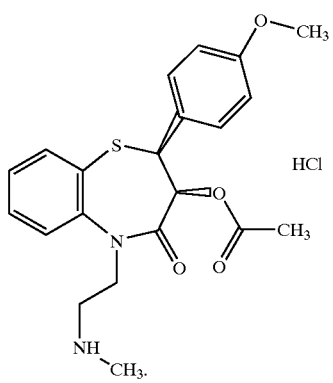

19. The method according to claim 15 wherein said compound has the formula

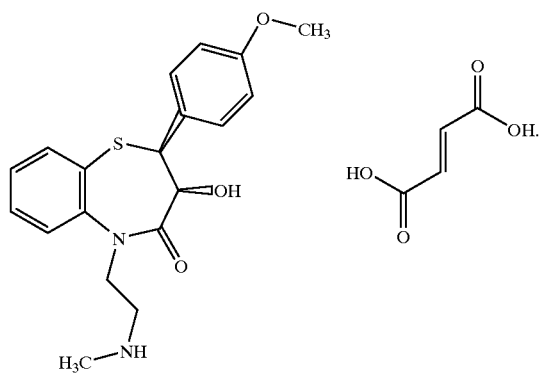

20. The method according to claim 15, further comprising preparing a medicament with said compound;
  said medicament being administrable orally, intramuscularly, intravenously, intra-ocularly, or in the form of eye drops.

* * * * *